US011215568B2

(12) United States Patent
Alvarez

(10) Patent No.: US 11,215,568 B2
(45) Date of Patent: Jan. 4, 2022

(54) SYSTEM FOR PERFORMING MICROWAVE MEASUREMENTS OF SAMPLES UNDER CONFINING PRESSURE

(71) Applicant: Saudi Arabian Oil Company, Dhahran (SA)

(72) Inventor: Jose Oliverio Alvarez, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 73 days.

(21) Appl. No.: 16/410,634

(22) Filed: May 13, 2019

(65) Prior Publication Data
US 2019/0346378 A1 Nov. 14, 2019

Related U.S. Application Data

(60) Provisional application No. 62/670,963, filed on May 14, 2018.

(51) Int. Cl.
*G01N 22/00* (2006.01)
*F16K 17/00* (2006.01)
*G01L 19/00* (2006.01)
*H01P 7/04* (2006.01)

(52) U.S. Cl.
CPC ............ *G01N 22/00* (2013.01); *F16K 17/00* (2013.01); *G01L 2019/0053* (2013.01); *H01P 7/04* (2013.01)

(58) Field of Classification Search
CPC . G01N 22/00; F16K 17/00; G01L 2019/0053; H01P 7/04
See application file for complete search history.

(56) References Cited

U.S. PATENT DOCUMENTS

| 4,479,070 A * | 10/1984 | Frische ................. G01L 9/0022 310/338 |
| 7,628,058 B2 | 12/2009 | Vinci |
| 2006/0049215 A1 * | 3/2006 | Lim ..................... B65D 83/663 222/402.1 |

(Continued)

OTHER PUBLICATIONS

GCC Examination Report issued in Gulf Cooperation Council Application GC 2019-37571 dated Aug. 31, 2020, 5 pages.

(Continued)

*Primary Examiner* — Tung X Nguyen
*Assistant Examiner* — Feba Pothen
(74) *Attorney, Agent, or Firm* — Fish & Richardson P.C.

(57) ABSTRACT

A pressure cell system includes a pressure cell configured to house a sample within inner walls of the pressure cell. An injection system is configured to inject an injectable medium into the pressure cell in a gap between the sample and the inner walls. A heating element is configured to provide heat to the injectable medium in the pressure cell. A pressure gauge is configured to measure pressure inside the pressure cell. A temperature gauge is configured to measure temperature in the pressure cell. A top is configured to provide a pressure resistant lid on the pressure cell. A coaxial resonator system is configured to capture microwave measurements of the sample at different temperatures and pressures after the sample is placed inside of the pressure cell, a top of the pressure cell is closed, and after the injectable medium is injected into the pressure cell in the gap.

18 Claims, 4 Drawing Sheets

(56) References Cited

U.S. PATENT DOCUMENTS

| | | | | |
|---|---|---|---|---|
| 2013/0009048 A1* | 1/2013 | Xie | ............. | G01N 21/33 |
| | | | | 250/256 |
| 2013/0125630 A1* | 5/2013 | Collins | ............. | E21B 43/20 |
| | | | | 73/64.56 |
| 2016/0169720 A1* | 6/2016 | Xie | ............. | G01F 1/74 |
| | | | | 73/861.11 |

OTHER PUBLICATIONS

International Search Report and Written Opinion issued in International Application No. PCT/US2019/031966 dated Nov. 7, 2019, 18 pages.

Oliverio et al., "Dielectric characterization of geochemical properties of crude oils and gas condensate at 25degrees C.," 2017 IEEE International Geoscience and Remote Sensing Symposium (IGARSS), IEEE, Jan. 23, 2017, 4 pages.

Stankowski et al., "Microwave resonators for EPR studies at high hydrostatic pressure," Review of Scientific Instruments, vol. 47, No. 1, Jan. 1, 1976, 3 pages.

"Anton-Paar Pressure Cell Manual," Pressure Cell PR170/Ti/XL and PR170/Ha/XL, Jul. 2017, 34 pages.

Aakre et al., "Conductivity and Permittivity of Midel 7131: Effect of Temperature, Moisture Content, Hydrostatic Pressure and Elextric Field," IEEE Transactions on Dielectrics and Electrical Insulation, vol. 23, No. 5, Oct. 2016, 8 pages.

Garcia-Banos et al., "Noninvasive Monitoring of Polymer Curing Reactions by Dielectrometry," IEEE Sensors Journal, vol. 11, No. 1, Jan. 2011, 9 pages.

rayoteksightwindows.com' [online], "High Pressure Flow Cell Signt Window," available on or before Mar. 2, 2018, retrieved on May 17, 2019, retrieved from URL <https://rayoteksightwindows.com/products/flowcell-sight-glass-windows-en.html>, 1 page.

GCC Examination Report issued in Gulf Cooperation Council Appln. No. GC 2019-37571, dated Feb. 8, 2020, 3 pages.

* cited by examiner

SYSTEM FOR PERFORMING MICROWAVE MEASUREMENTS OF SAMPLES UNDER CONFINING PRESSURE

CROSS-REFERENCE TO RELATED APPLICATIONS

This application is a conversion of Provisional Application No. 62/670,963, filed on May 14, 2018, and is hereby incorporated by reference in its entirety.

BACKGROUND

The present disclosure applies to measuring properties of materials. In the oil and gas industry, for example, measuring certain properties of materials in downhole conditions may be a major challenge. Some conventional high-pressure cells exist for making measurements, but these solutions typically either put the sample under pressure to measure maximum shear stresses or perform only a limited number of measurements. If high-frequency measurements may be made at all, the values are limited to only one frequency and temperature.

SUMMARY

The present disclosure describes techniques that may be used for performing microwave measurements of samples under confining pressure. In some embodiments, a pressure cell system may include: a pressure cell configured to house a sample within inner walls of the pressure cell; an injection system configured to inject an injectable medium into the pressure cell in a gap between the sample and the inner walls; a heating element configured to provide heat to the injectable medium in the pressure cell; a pressure gauge configured to measure pressure inside the pressure cell; a temperature gauge configured to measure temperature in the pressure cell; a top configured to provide a pressure resistant lid on the pressure cell; and a coaxial resonator system configured to capture microwave measurements of the sample at different combinations of temperatures and pressures, the microwave measurements captured after the sample is placed inside of the pressure cell, a top of the pressure cell is closed, and after the injectable medium is injected into the pressure cell in the gap between the sample and the inner walls.

In one embodiment, the system may be used in a computer-implemented method; a non-transitory, computer-readable medium storing computer-readable instructions to perform the computer-implemented method; and a computer-implemented system including a computer memory interoperably coupled with a hardware processor configured to perform the computer-implemented method/the instructions stored on the non-transitory, computer-readable medium. Also presented herein is a method including the following steps: housing, by a pressure cell in a pressure cell system, a sample within inner walls of a pressure cell; injecting, by an injection system in the pressure cell system, an injectable medium into the pressure cell in a gap between the sample and the inner walls; heating, by a heating element in the pressure cell system, the injectable medium in the pressure cell; measuring, by a pressure gauge in the pressure cell system, pressure inside the pressure cell; measuring, by a temperature gauge in the pressure cell system, a temperature in the pressure cell; and capturing, by a coaxial resonator system in the pressure cell system, microwave permittivity measurements of the sample at different combinations of temperatures and pressures, where the microwave measurements are captured after the sample is placed inside of the pressure cell and a top including a pressure resistant lid is closed on the pressure cell, after the injectable medium is injected into the pressure cell in the gap between the sample and the inner walls, and after heat is optionally provided by the heating element to the injectable medium in the pressure cell.

The pressure cell system and methods described herein may be used to realize one or more of the following advantages. First, using a pressure cell may allow microwave properties, such as permittivity, to be measured at various pressures, not just an atmospheric pressure. Second, converting quartz or sapphire windows into a short-circuited coaxial probe for a coaxial resonator may simplify manufacturing.

The details of one or more embodiments of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Presented herein are techniques for performing microwave measurements of samples under confining pressure. Various modifications, alterations, and permutations of the disclosed embodiments may be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Figure 1:
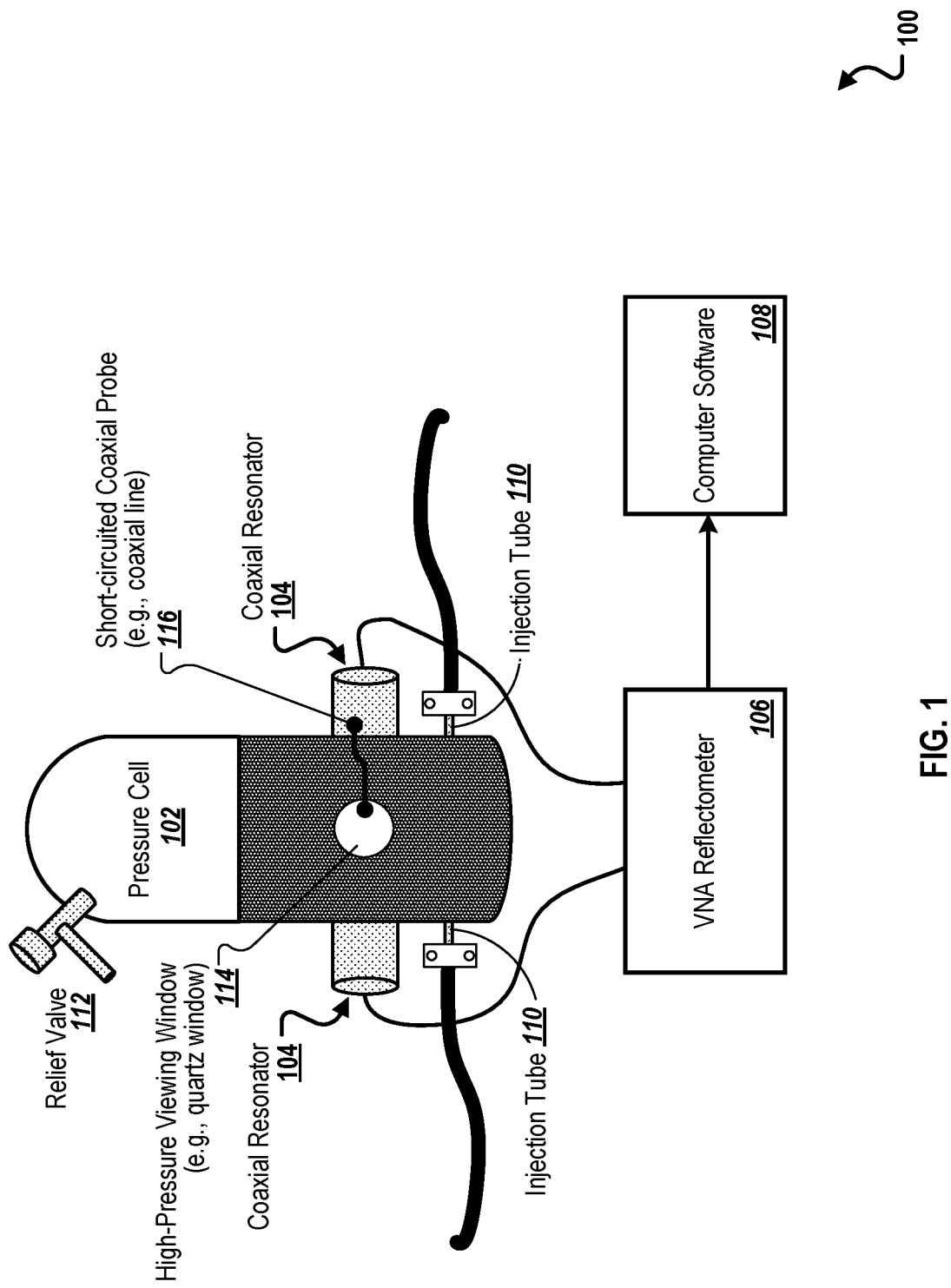
FIG. 1 is a block diagram showing an example of a pressure cell system, according to some embodiments of the present disclosure.

FIG. 1 is a block diagram showing an example of a pressure cell system 100, according to some embodiments of the present disclosure. The pressure cell system 100 includes a pressure cell 102 that may be used to perform measurements of samples that are placed in the pressure cell 102.

In some embodiments, the pressure cell 102 may be a confining pressure cell that is modified to allow for microwave measurements of the $S_{11}$ parameters at different pressures and temperatures. A basic implementation consists of measuring the complex permittivity of a fluid or fluids filling the pressure cell. A modification may be based, at least in part, on designs for microwave sensor systems for noninvasive monitoring of curing processes.

In some embodiments, the confining pressure cell may be modified to create the pressure cell 102. In one embodiment, an open coaxial probe may be added as part of the inner walls of the confining pressure cell by using current available technology of glass/metal fusion, for example, including quartz and metal. A high-pressure viewing window may be combined with a short-circuited coaxial probe, providing a coaxial resonator. One or more fixed open coaxial probes may be integrated within a coaxial resonator system that may include, for example, at least one coaxial resonator 104. Instead of using a container for the sample, a thin film of oil or gas may be used. Additional oil or gas may be added once the cell is closed. The additional injection of oil/gas is all that is needed to measure the permittivity of a sample under pressure at several frequencies.

The pressure cell may be made of stainless steel and may have cylindrical or cubic shape. A system that includes the pressure cell may include a liquid and/or gas injection systems, a pressure gauge, a heating element, and a temperature gauge. The internal diameter pressure cell may be just slightly larger than that of solid samples. Gap sizes may vary from 1 micron to 1 centimeter, depending on the fluid used to fill the gap and pressurized with. For example, after a solid sample is placed inside the pressure cell, the gap between walls of the sample and the cell walls of the pressure cell may be filled with a fluid (such as oil or water) or air. A top on the pressure cell may include a pressure-resistant lid. After the top is closed, additional fluid, for example, may be injected until the desired unconfined pressured inside the pressure cell is reached.

If the sample is gas, the pressure cell may first be closed, and the gas may be injected (removing air inside of the pressure cell), or a vacuum may be created in the cell before filling the pressure cell with the desired gas. The gas may be injected until a desired pressure and temperature is reached.

The internal walls of the pressure cell may have at least one quartz or sapphire window having a circular shape and including a central conductor. The dimensions of the central conductor diameter and the outer diameter of the quartz window may create a coaxial line of a desired impedance, such as 50 ohm.

In some embodiments, the pressure cell 102 can be made of titanium or a mixture of metals. In some embodiments, the inner walls of the coaxial line and surface of the inner conductor may be coated with a silver or gold bath for increased conductivity, such as before the quartz is added.

The coaxial line at one end of a coaxial resonator may be ended by a short circuit (wall), and the coaxial line may be connected to a vector network analyzer (VNA) 106 or a miniaturized reflectometer. The VNA or reflectometer 106 may compute the resonance frequency and quality factor, and from those values, the computer may obtain the permittivity. This may facilitate the development of downhole tools that may be used to characterize different geochemical (rock or fluid) and geomechanical (rock or shale) properties. The coaxial sensor may also work for fluid samples under pressure. Different kinds of software may be used, depending on the implementation of the pressure cell system.

The output of the VNA/reflectometer 106, the $S_{11}$ parameter measurements of a sample in the pressure cell 102, may be provided to computer software 108 to obtain the complex permittivity of the sample at a particular frequency. For example, a user of a computing device on which the computer software 108 executes may review information about pressure, temperature, and microwave measurements in a graphical user interface (GUI) provided by the computer software 108. The computer software 108 may provide controls that the user may use to set a desired pressure and a desired temperature. An injection system and a heating element in the pressure cell 102 may attain and maintain the desired pressure and the desired temperature.

The pressure cell 102 can include at least two injection tubes 110 that are each capable for use in injecting gas or fluid into the pressure cell 102. In some embodiments, the pressure cell 102 can include a relief valve 112 that can be connected to a large sealed container for the recovery of fluid that passes through the relief valve 112. The relief valve 112 can include a pressure gauge for indicating the pressure inside the pressure cell 102. Release of gas or fluid can occur, for example, when the pressure cell 102 attains a pressure above a threshold. In some embodiments, the relief valve 112 can be activated manually. One of the injectors of the pressure cell 102 can be a fluid/pressure relief system. A high-pressure viewing window 114 of the pressure cell 102 includes a short-circuited coaxial probe 116 connected to the coaxial resonator 104.

Figure 2:
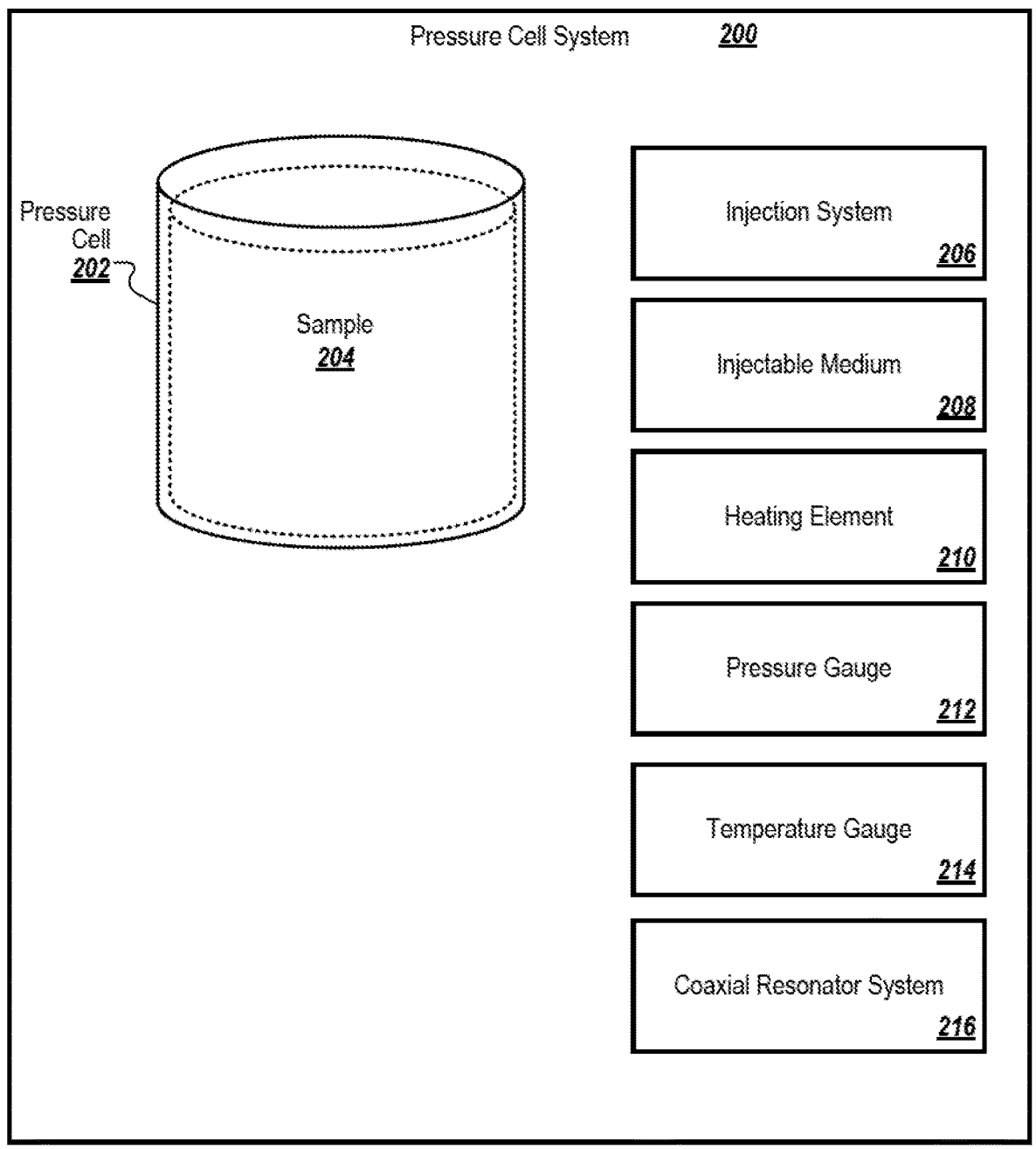
FIG. 2 is a block diagram showing an example of a pressure cell system, according to some embodiments of the present disclosure.

FIG. 2 is a block diagram showing an example of a pressure cell system 200, according to some embodiments of the present disclosure. The pressure cell system 200 may be used to implement features of the pressure cell system 100.

As shown in FIG. 2, the pressure cell system 200 includes a pressure cell 202 that is configured to house a sample 204 within inner walls of the pressure cell 202. The pressure cell 202 may be sized so that a solid sample 204 just barely fits within the inner walls of the pressure cell 202.

An injection system 206 may be used to inject an injectable medium 208 into the pressure cell 202. Injection may occur, for example, in a gap between the sample 204 and the inner walls. Injection may occur at one or multiple injection points. Different sized pressure cell 202 may be made to fit different sizes of samples 204.

A heating element 210 may be used to provide heat to the injectable medium 208 in the pressure cell 202. The heating element 210 may include multiple elements so that an even distribution of heat may be applied in an efficient way.

The pressure cell system 200 may include different types of gauges and other monitoring components that may track and report conditions in the pressure cell 202 in real time. For example, a pressure gauge 212 may be used to measure pressure inside the pressure cell 202. A temperature gauge 214 may be used to measure temperature in the pressure cell 202. There may be multiple temperature gauges 214, and the temperatures of each gauge may be reported. In some embodiments, average and maximum temperatures may be determined from the multiple temperature gauges 214. The pressure cell 202 includes a top that may serve as a pressure-resistant lid on the pressure cell 202.

A coaxial resonator system 216 may be configured to capture microwave measurements ($S_{11}$ parameter) of the sample at different combinations of temperatures and pressures. The microwave measurements may be captured after the sample 204 is placed inside of the pressure cell 202 and a top of the pressure cell 202 is closed. After the injectable medium 208 is injected into the pressure cell 202 in the gap between the sample 204 and the inner walls, heat may be provided by the heating element 210 to the injectable medium 208 in the pressure cell 202.

Figure 3:
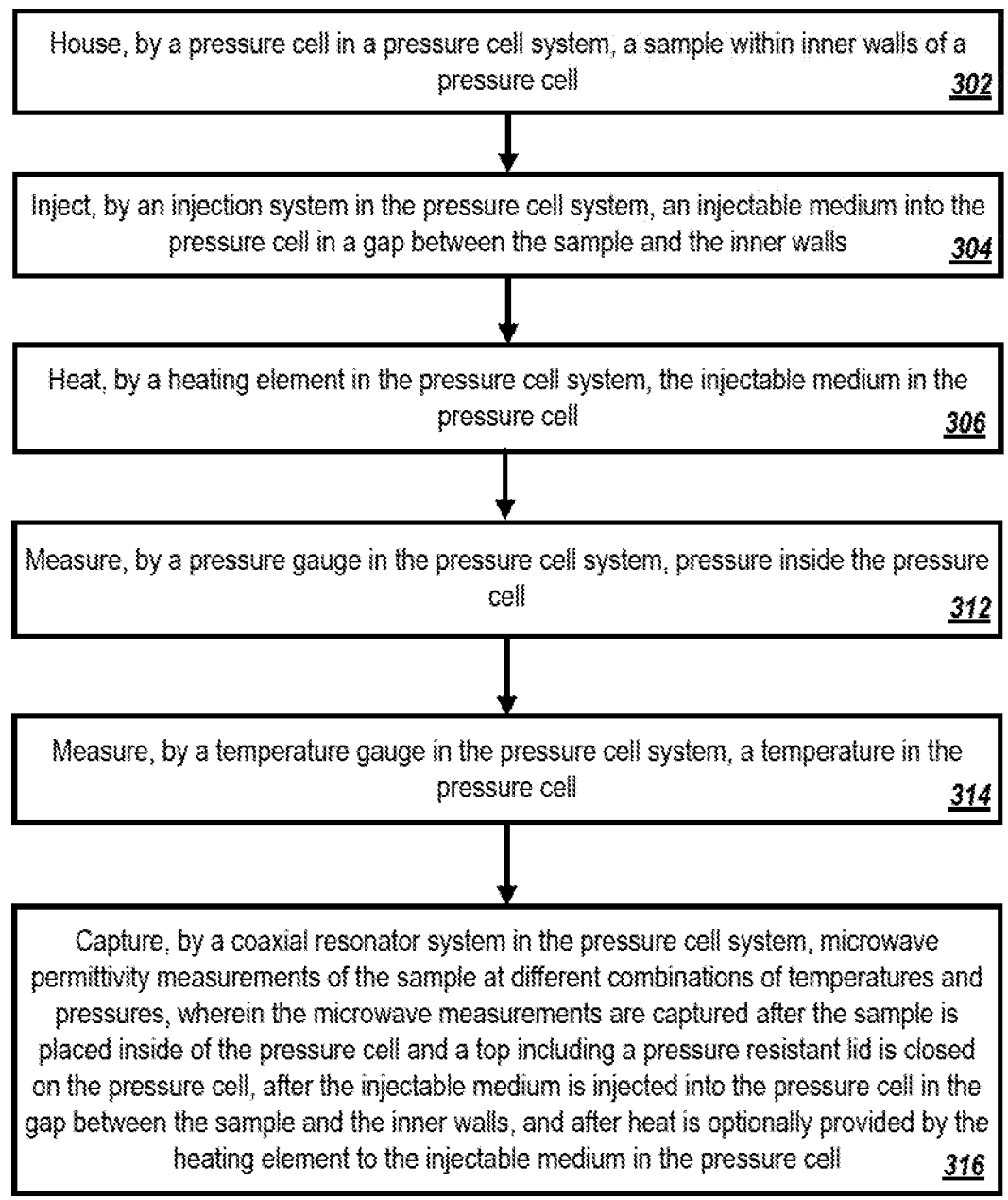
FIG. 3 is a flowchart of an example method for performing microwave measurements of samples under confining pressure, according to some embodiments of the present disclosure.
Figure 3:

FIG. 3 is a flowchart of an example method 300 for performing microwave measurements of samples under confining pressure, according to some embodiments of the present disclosure. For clarity of presentation, the description that follows generally describes method 300 in the context of the other figures in this description. However, it will be understood that method 300 may be performed, for example, by any suitable system, environment, software, and hardware, or a combination of systems, environments, software, and hardware, as appropriate. In some embodiments, various steps of method 300 may be run in parallel, in combination, in loops, or in any order.

At 302, a pressure cell in a pressure cell system houses a sample within inner walls of a pressure cell. For example, the pressure cell 202 may house the sample 204. From 302, method 300 proceeds to 304.

At 304, an injection system in the pressure cell system injects an injectable medium into the pressure cell in a gap between the sample and the inner walls. As an example, the injection system 206 may inject the injectable medium 208, such as a fluid or a gas, into the pressure cell 202. The injectable medium 208 may be injected into a gap between the sample 204 and inner walls of the pressure cell 202. From 304, method 300 proceeds to 306.

At 306, a heating element in the pressure cell system heats the injectable medium in the pressure cell. For example, the heating element 210 may heat the pressure cell 202, such as by including heating elements at various locations on the inner walls of the pressure cell 202. From 306, method 300 proceeds to 312.

At 312, a pressure gauge in the pressure cell system measures pressure inside the pressure cell. As an example, the pressure gauge 212 may measure pressure at one or more locations inside the pressure cell 202. If the sample 204 is a fluid, then the injectable medium 208 is a fluid for which permittivity is measured. From 312, method 300 proceeds to 314.

At 314, a temperature gauge in the pressure cell system measures a temperature in the pressure cell. For example, the temperature gauge 214 may measure temperature at one or more locations inside the pressure cell 202. From 314, method 300 proceeds to 316.

At 316, a coaxial resonator system in the pressure cell system captures microwave measurements of the sample at different combinations of temperatures and pressures. For example, the coaxial resonator system 216 may capture microwave measurements after the sample 204 is placed inside of the pressure cell 202 and the top of the pressure cell 202 is closed on the pressure cell. The microwave measurements may be captured after the injectable medium is injected into the pressure cell 202 in the gap between the sample 204 and the inner walls. Heat may optionally be provided by the heating element 210 to the injectable medium 208 in the pressure cell 202. After 316, method 300 stops.

In some embodiments, method 300 may be used (or modified for use) in drilling applications, for example, for gas kick characterization. For example, if a cell is filled with drill mud at a specific pressure, gas or a mix of gases may be injected for characterization of a gas kick in drilling operations.

Figure 4:
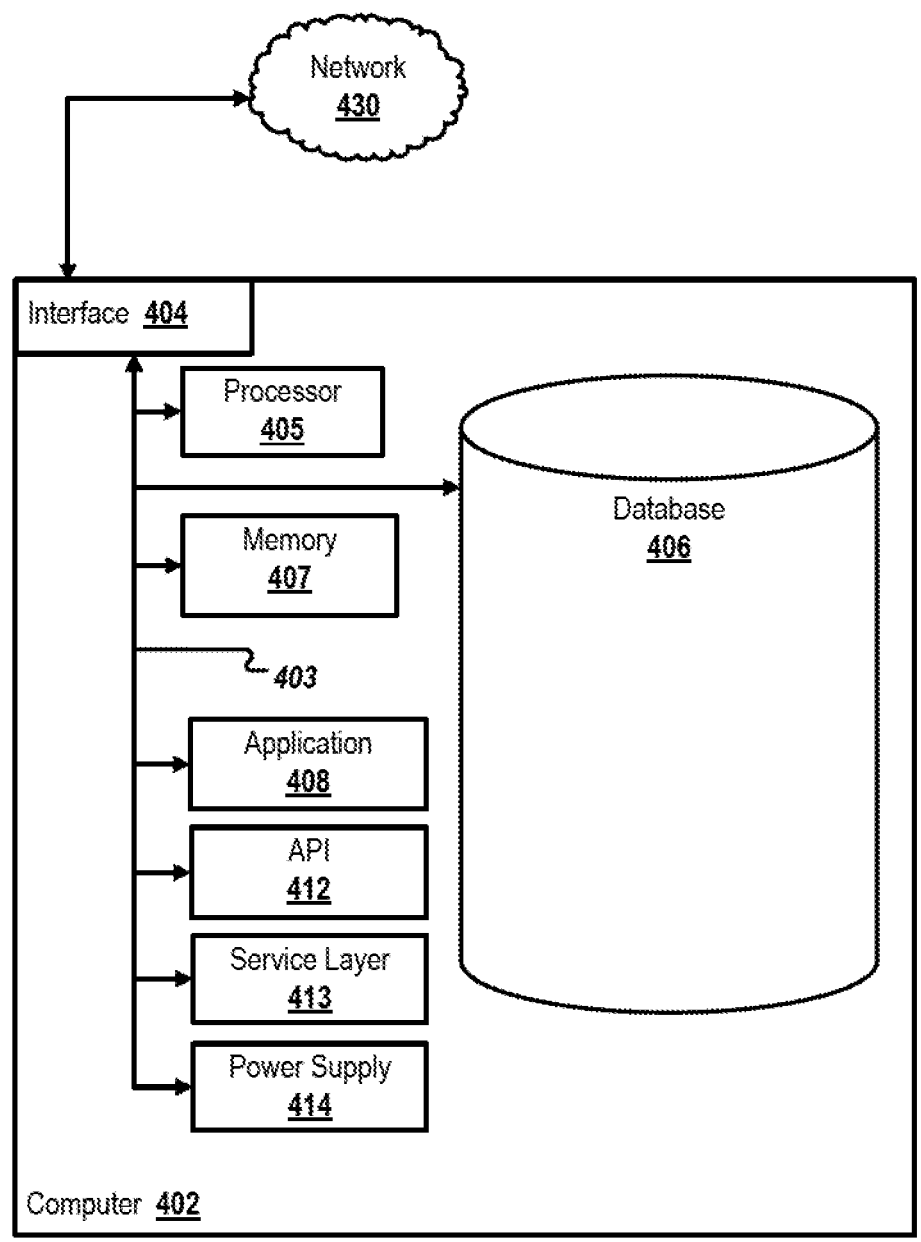
FIG. 4 is a block diagram illustrating an example computer system used to provide computational functionalities associated with described algorithms, methods, functions, processes, flows, and procedures as described in the instant disclosure, according to some embodiments of the present disclosure.

FIG. 4 is a block diagram of an example computer system 400 used to provide computational functionalities associated with described algorithms, methods, functions, processes, flows, and procedures, as described in the instant disclosure, according to some embodiments of the present disclosure. The illustrated computer 402 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 402 may comprise a computer that includes an input device, such as a keypad, keyboard, touch screen, or other device that may accept user information, and an output device that conveys information associated with the operation of the computer 402, including digital data, visual, or audio information (or a combination of information), or a graphical-type user interface (UI) (or GUI).

The computer 402 may serve in a role as a client, network component, a server, a database or other persistency, or any other component (or a combination of roles) of a computer system for performing the subject matter described in the instant disclosure. The illustrated computer 402 is communicably coupled with a network 430. In some embodiments, one or more components of the computer 402 may be configured to operate within environments, including cloud-computing-based, local, global, or other environment (or a combination of environments).

At a high level, the computer 402 is an electronic computing device operable to receive, transmit, process, store, or manage data and information associated with the described subject matter. According to some embodiments, the computer 402 may also include or be communicably coupled with an application server, email server, web server, caching server, streaming data server, or other server (or a combination of servers).

The computer 402 may receive requests over network 430 from a client application (for example, executing on another computer 402) and respond to the received requests by processing the received requests using an appropriate software application(s). In addition, requests may also be sent to the computer 402 from internal users (for example, from a command console or by other appropriate access method), external or third-parties, other automated applications, as well as any other appropriate entities, individuals, systems, or computers.

Each of the components of the computer 402 may communicate using a system bus 403. In some embodiments, any or all of the components of the computer 402, hardware or software (or a combination of both hardware and software), may interface with each other or the interface 404 (or a combination of both), over the system bus 403 using an application programming interface (API) 412 or a service layer 413 (or a combination of the API 412 and service layer 413). The API 412 may include specifications for routines, data structures, and object classes. The API 412 may be either computer-language independent or dependent and refer to a complete interface, a single function, or even a set of APIs. The service layer 413 provides software services to the computer 402 or other components (whether or not illustrated) that are communicably coupled to the computer 402. The functionality of the computer 402 may be accessible for all service consumers using this service layer. Software services, such as those provided by the service layer 413, provide reusable, defined functionalities through a defined interface. For example, the interface may be software written in JAVA, C++, or other suitable language providing data in extensible markup language (XML) format or other suitable format. While illustrated as an integrated component of the computer 402, alternative implementations may illustrate the API 412 or the service layer 413 as stand-alone components in relation to other components of the computer 402 or other components (whether or not illustrated) that are communicably coupled to the computer 402. Moreover, any or all parts of the API 412 or the service layer 413 may be implemented as child or sub-modules of another software module, enterprise application, or hardware module without departing from the scope of this disclosure.

The computer 402 includes an interface 404. Although illustrated as a single interface 404 in FIG. 4, two or more interfaces 404 may be used according to particular needs, desires, or particular implementations of the computer 402. The interface 404 is used by the computer 402 for communicating with other systems that are connected to the network 430 (whether illustrated or not) in a distributed environment. Generally, the interface 404 comprises logic encoded in software or hardware (or a combination of software and hardware) and is operable to communicate with the network 430. More specifically, the interface 404 may comprise software supporting one or more communication protocols associated with communications such that the network 430 or interface's hardware is operable to communicate physical signals within and outside of the illustrated computer 402.

The computer 402 includes a processor 405. Although illustrated as a single processor 405 in FIG. 4, two or more processors may be used according to particular needs, desires, or particular implementations of the computer 402. Generally, the processor 405 executes instructions and manipulates data to perform the operations of the computer 402 and any algorithms, methods, functions, processes, flows, and procedures as described in the instant disclosure.

The computer 402 also includes a database 406 that may hold data for the computer 402 or other components (or a combination of both) that may be connected to the network 430 (whether illustrated or not). For example, database 406 may be an in-memory, conventional, or other type of database storing data consistent with this disclosure. In some embodiments, database 406 may be a combination of two or more different database types (for example, a hybrid in-memory and conventional database) according to particular needs, desires, or particular implementations of the computer 402 and the described functionality. Although illustrated as a single database 406 in FIG. 4, two or more databases (of the same or combination of types) may be used according to particular needs, desires, or particular implementations of the computer 402 and the described functionality. While database 406 is illustrated as an integral component of the computer 402, in alternative implementations, database 406 may be external to the computer 402.

The computer 402 also includes a memory 407 that may hold data for the computer 402 or other components (or a combination of both) that may be connected to the network 430 (whether illustrated or not). Memory 407 may store any data consistent with this disclosure. In some embodiments, memory 407 may be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same or combination of types) may be used according to particular needs, desires, or particular implementations of the computer 402 and the described functionality. While memory 407 is illustrated as an integral component of the computer 402, in alternative implementations, memory 407 may be external to the computer 402.

The application 408 is an algorithmic software engine providing functionality according to particular needs, desires, or particular implementations of the computer 402, particularly with respect to functionality described in this disclosure. For example, application 408 may serve as one or more components, modules, or applications. Further, although illustrated as a single application 408, the application 408 may be implemented as multiple applications 408 on the computer 402. In addition, although illustrated as integral to the computer 402, in alternative implementations, the application 408 may be external to the computer 402.

The computer 402 may also include a power supply 414. The power supply 414 may include a rechargeable or non-rechargeable battery that may be configured to be either user- or non-user-replaceable. In some embodiments, the power supply 414 may include power-conversion or management circuits (including recharging, standby, or other power management functionality). In some embodiments, the power-supply 414 may include a power plug to allow the computer 402 to be plugged into a wall socket or other power source to, for example, power the computer 402 or recharge a rechargeable battery.

There may be any number of computers 402 associated with, or external to, a computer system containing computer 402, each computer 402 communicating over network 430. Further, the term "client," "user," and other appropriate terminology may be used interchangeably, as appropriate, without departing from the scope of this disclosure. Moreover, this disclosure contemplates that many users may use one computer 402, or that one user may use multiple computers 402.

Described embodiments may include one or more features, alone or in combination.

For example, in a first implementation, a pressure cell system may include: a pressure cell configured to house a sample within inner walls of the pressure cell; an injection system configured to inject an injectable medium into the pressure cell in a gap between the sample and the inner walls; a heating element configured to provide heat to the injectable medium in the pressure cell; a pressure gauge configured to measure pressure inside the pressure cell; a temperature gauge configured to measure temperature in the pressure cell; a top configured to provide a pressure resistant lid on the pressure cell; and a coaxial resonator system configured to capture microwave measurements of the sample at different combinations of temperatures and pressures, the microwave measurements captured after the sample is placed inside of the pressure cell, a top of the pressure cell is closed, and after the injectable medium is injected into the pressure cell in the gap between the sample and the inner walls.

The foregoing and other described embodiments may each, optionally, include one or more of the following features:

A first feature, combinable with any of the following features, where the coaxial resonator system includes coaxial probes embedded in the inner walls of the pressure cell.

A second feature, combinable with any of the previous or following features, where the coaxial probes are embedded in the inner walls using glass-metal fusion using quartz and a metal.

A third feature, combinable with any of the previous or following features, further including controls configured to allow setting, by a user, of a desired pressure and a desired temperature, where the injection system and the heating element are further configured to attain and maintain the desired pressure and the desired temperature.

A fourth feature, combinable with any of the previous or following features, further including a user interface configured to receive user inputs from a user and to display information about the pressure cell system, including pressure information, temperature information, and captured microwave measurements of the sample.

A fifth feature, combinable with any of the previous or following features, where the pressure cell is made of stainless steel, where a cross-section of the pressure cell has a cylindrical shape or a square shape, and where the inner walls are sized slightly larger than the sample.

A sixth feature, combinable with any of the previous or following features, where the injectable medium is a fluid or a gas.

A seventh feature, combinable with any of the previous or following features, where a high-pressure viewing window of the pressure cell is converted into a short-circuited coaxial probe or a coaxial resonator.

An eighth feature, combinable with any of the previous or following features, where the sample is a fluid sample, where, after the pressure cell is closed, the fluid sample is injected into the pressure cell to remove air in the pressure cell, and where injection of the gas sample continues until a desired pressure/temperature is attained.

A ninth feature, combinable with any of the previous or following features, where the sample is a fluid sample, where, after the pressure cell is closed, a vacuum is created in the pressure cell, and where the fluid sample is injected until a desired pressure/temperature is attained.

A tenth feature, combinable with any of the previous or following features, where the internal walls of the pressure cell include at least one quartz or sapphire filled, short-circuited, coaxial line.

An eleventh feature, combinable with any of the previous or following features, where the dimensions of the central conductor diameter and the outer diameter of the quartz window make a coaxial line of a desired impedance.

A twelfth feature, combinable with any of the previous or following features, where one end of the coaxial resonator includes the coaxial line and is ended by a short circuit at an inner wall of the pressure cell, where the coaxial resonator is connected to one of a vector network analyzer or a miniaturized reflectometer, and where the coaxial resonator is configured to measure an $S_{11}$ reflection coefficient as a function of frequency for a given pressure and temperature from which an application computes a complex permittivity based on a resonant frequency and a quality factor.

A thirteenth feature, combinable with any of the previous or following features, where the heating element provides heat to the injectable medium in the pressure cell before at least one of the microwave measurements is captured.

In a second implementation, a computer-implemented method including: housing, by a pressure cell in a pressure cell system, a sample within inner walls of a pressure cell; injecting, by an injection system in the pressure cell system, an injectable medium into the pressure cell in a gap between the sample and the inner walls; heating, by a heating element in the pressure cell system, the injectable medium in the pressure cell; measuring, by a pressure gauge in the pressure cell system, pressure inside the pressure cell; measuring, by a temperature gauge in the pressure cell system, a temperature in the pressure cell; and capturing, by a coaxial resonator system in the pressure cell system, microwave permittivity measurements of the sample at different combinations of temperatures and pressures, where the microwave measurements are captured after the sample is placed inside of the pressure cell and a top including a pressure resistant lid is closed on the pressure cell, after the injectable medium is injected into the pressure cell in the gap between the sample and the inner walls, and after heat is optionally provided by the heating element to the injectable medium in the pressure cell.

The foregoing and other described implementations may each, optionally, include one or more of the following features:

A first feature, combinable with any of the previous or following features, further including, when the sample is a fluid, measuring a permittivity of the injectable medium.

A second feature, combinable with any of the previous or following features, where the coaxial resonator system includes coaxial probes embedded in the inner walls of the pressure cell.

In a third implementation, a non-transitory, computer-readable medium storing one or more instructions executable by a computer system to perform operations including: housing, by a pressure cell in a pressure cell system, a sample within inner walls of a pressure cell; injecting, by an injection system in the pressure cell system, an injectable medium into the pressure cell in a gap between the sample and the inner walls; heating, by a heating element in the pressure cell system, the injectable medium in the pressure cell; measuring, by a pressure gauge in the pressure cell system, pressure inside the pressure cell; measuring, by a temperature gauge in the pressure cell system, a temperature in the pressure cell; and capturing, by a coaxial resonator system in the pressure cell system, microwave permittivity measurements of the sample at different combinations of temperatures and pressures, where the microwave measurements are captured after the sample is placed inside of the pressure cell and a top including a pressure resistant lid is closed on the pressure cell, after the injectable medium is injected into the pressure cell in the gap between the sample and the inner walls, and after heat is optionally provided by the heating element to the injectable medium in the pressure cell.

The foregoing and other described implementations may each, optionally, include one or more of the following features:

A first feature, combinable with any of the previous or following features, further including, when the sample is a fluid, measuring a permittivity of the injectable medium.

A second feature, combinable with any of the previous or following features, where the coaxial resonator system includes coaxial probes embedded in the inner walls of the pressure cell.

Implementations of the subject matter and the functional operations described in this specification may be implemented in digital electronic circuitry, in tangibly embodied computer software or firmware, in computer hardware, including the structures disclosed in this specification and their structural equivalents, or in combinations of one or more of them. Software implementations of the described subject matter may be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions may be encoded in/on an artificially generated propagated signal, for example, a machine-generated electrical, optical, or electromagnetic signal that is generated to encode information for transmission to suitable receiver apparatus for execution by a data processing apparatus. The computer-storage medium may be a machine-readable storage device, a machine-readable storage substrate, a random or serial access memory device, or a combination of computer-storage mediums.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus may also be, or further include special purpose logic circuitry, for example, a central processing unit (CPU), an field programmable gate array (FPGA), or an application-specific integrated circuit (ASIC). In some embodiments, the data processing apparatus or special purpose logic circuitry (or a combination of the data processing apparatus or special purpose logic circuitry) may be hardware- or software-based (or a combination of both hardware- and software-based). The apparatus may optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, IOS, or any other suitable conventional operating system.

A computer program, which may also be referred to or described as a program, software, a software application, a module, a software module, a script, or code may be written in any form of programming language, including compiled or interpreted languages, or declarative or procedural languages, and it may be deployed in any form, including as a stand-alone program or as a module, component, subroutine, or other unit suitable for use in a computing environment. A computer program may, but need not, correspond to a file in a file system. A program may be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program may be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components may be combined into single components, as appropriate. Thresholds used to make computational determinations may be statically, dynamically, or both statically and dynamically determined.

The methods, processes, or logic flows described in this specification may be performed by one or more programmable computers executing one or more computer programs to perform functions by operating on input data and generating output. The methods, processes, or logic flows may also be performed by, and apparatus may also be implemented as, special purpose logic circuitry, for example, a CPU, an FPGA, or an ASIC.

Computers suitable for the execution of a computer program may be based on general or special purpose microprocessors, both, or any other kind of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer may be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data includes all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital video disc (DVD), CD-ROM, DVD+/-R, DVD-RAM, DVD-ROM, HD-DVD, and BLURAY, and other optical memory technologies. The memory may store various objects or data, including caches, classes, frameworks, applications, modules, backup data, jobs, web pages, web page templates, data structures, database tables, repositories storing dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory may be supplemented by, or incorporated in, special purpose logic circuitry.

To provide for interaction with a user, implementations of the subject matter described in this specification may be implemented on a computer having a display device, for example, a cathode ray tube (CRT), liquid crystal display (LCD), light-emitting diode (LED), or plasma monitor, for displaying information to the user and a keyboard and a pointing device, for example, a mouse, trackball, or trackpad by which the user may provide input to the computer. Input may also be provided to the computer using a touchscreen, such as a tablet computer surface with pressure sensitivity, a multi-touch screen using capacitive or electric sensing, or other type of touchscreen. Other kinds of devices may be used to provide for interaction with a user as well; for example, feedback provided to the user may be any form of sensory feedback, for example, visual feedback, auditory feedback, or tactile feedback; and input from the user may be received in any form, including acoustic, speech, or tactile input. In addition, a computer may interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. These and other UI elements may be related to or represent the functions of the web browser.

Implementations of the subject matter described in this specification may be implemented in a computing system that includes a back-end component, for example, as a data server, or that includes a middleware component, for example, an application server, or that includes a front-end component, for example, a client computer having a graphical user interface or a Web browser through which a user may interact with some embodiments of the subject matter described in this specification, or any combination of one or more such back-end, middleware, or front-end components. The components of the system may be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses.

The computing system may include clients and servers. A client and server are generally remote from each other and typically interact through a communication network. The relationship of client and server arises by virtue of computer programs running on the respective computers and having a client-server relationship to each other.

Cluster file system involved in this invention may be any file system type accessible from multiple servers for read and update. Locking or consistency tracking is not necessary in this invention since the locking of exchange file system may be done at application layer. Furthermore, Unicode data files are different from non-Unicode data files.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations may also be implemented, in combination, in a single implementation. Conversely, various features that are described in the context of a single implementation may also be implemented in multiple implementations, separately, or in any suitable sub-combination. Moreover, although previously described features may be described as acting in certain combinations and even initially claimed as such, one or more features from a claimed combination may, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems may generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A pressure cell system, comprising:
   a pressure cell configured to house a sample within inner walls of the pressure cell;
   an injection system configured to inject an injectable medium into the pressure cell in a gap between the sample and the inner walls;
   a heating element configured to provide heat to the injectable medium in the pressure cell;
   a pressure gauge configured to measure pressure inside the pressure cell;
   a pressure relief valve to release excess pressure above a specific threshold;
   a temperature gauge configured to measure temperature in the pressure cell;
   a top configured to provide a pressure resistant lid on the pressure cell;
   a high-pressure viewing window including a short-circuited coaxial probe connected to a coaxial resonator; and
   a coaxial resonator system configured to capture, using the short-circuited coaxial probe and the coaxial resonator, microwave measurements of the sample at different combinations of temperatures and pressures, the microwave measurements captured after the sample is placed inside of the pressure cell, a top of the pressure cell is closed, and after the injectable medium is injected into the pressure cell in the gap between the sample and the inner walls, wherein dimensions of a central conductor diameter and an outer diameter of a quartz window provide a coaxial line of a desired impedance of 50 ohm.

2. The pressure cell system of claim 1, wherein the short-circuited coaxial probe is embedded in the inner walls of the pressure cell.

3. The pressure cell system of claim 2, wherein the short-circuited coaxial probe is embedded in the inner walls using glass-metal fusion using quartz and a metal.

4. The pressure cell system of claim 1, further comprising controls configured to allow setting, by a user, of a desired pressure and a desired temperature, wherein the injection system and the heating element are further configured to attain and maintain the desired pressure and the desired temperature.

5. The pressure cell system of claim 1, further comprising a user interface configured to receive user inputs from a user and to display information about the pressure cell system, including pressure information, temperature information, and captured microwave measurements of the sample.

6. The pressure cell system of claim 1, wherein the pressure cell is made of stainless steel or titanium or any mix of metals, wherein a cross-section of the pressure cell has a cylindrical shape or a square shape, and wherein the inner walls are sized slightly larger than the sample.

7. The pressure cell system of claim 1, wherein the injectable medium is a fluid or a gas.

8. The pressure cell system of claim 1, wherein the sample is a gas sample, wherein, after the pressure cell is closed, the gas sample is injected into the pressure cell to remove air in the pressure cell, and wherein injection of the gas sample continues until a desired pressure/temperature is attained.

9. The pressure cell system of claim 1, wherein the sample is a fluid sample, wherein, after the pressure cell is closed, a vacuum is created in the pressure cell, and wherein the fluid sample is injected until a desired pressure/temperature is attained.

10. The pressure cell system of claim 1, wherein the inner walls of the pressure cell include at least one quartz or sapphire filled, short-circuited, coaxial line.

11. The pressure cell system of claim 1, wherein one end of the coaxial resonator includes the coaxial line and is ended by a short circuit at an inner wall of the pressure cell, wherein the coaxial resonator is connected to one of a vector network analyzer or a miniaturized reflectometer, and wherein the coaxial resonator is configured to measure an Si' reflection coefficient as a function of frequency for a given pressure and temperature from which an application computes a complex permittivity based on a resonant frequency and a quality factor.

12. The pressure cell system of claim 1, wherein the heating element provides heat to the injectable medium in the pressure cell before at least one of the microwave measurements is captured.

13. A computer-implemented method, comprising:
    housing, by a pressure cell in a pressure cell system, a sample within inner walls of a pressure cell;
    injecting, by an injection system in the pressure cell system, an injectable medium into the pressure cell in a gap between the sample and the inner walls;
    heating, by a heating element in the pressure cell system, the injectable medium in the pressure cell;
    measuring, by a pressure gauge in the pressure cell system, pressure inside the pressure cell;
    measuring, by a temperature gauge in the pressure cell system, a temperature in the pressure cell; and
    capturing, by a coaxial resonator system in the pressure cell system through a short-circuited coaxial probe included in a high-pressure viewing window and connected to a coaxial resonator, microwave permittivity measurements of the sample at different combinations of temperatures and pressures, wherein the microwave measurements are captured after the sample is placed inside of the pressure cell and a top including a pressure resistant lid is closed on the pressure cell, after the injectable medium is injected into the pressure cell in the gap between the sample and the inner walls, and after heat is optionally provided by the heating element to the injectable medium in the pressure cell, wherein dimensions of a central conductor diameter and an outer diameter of a quartz window provide a coaxial line of a desired impedance of 50 ohm.

14. The computer-implemented method of claim 13, further comprising, when the sample is a fluid, measuring a permittivity of the injectable medium.

15. The computer-implemented method of claim 13, wherein the short-circuited coaxial probe is embedded in the inner walls of the pressure cell.

16. A non-transitory, computer-readable medium storing one or more instructions executable by a computer system to perform operations comprising:
    housing, by a pressure cell in a pressure cell system, a sample within inner walls of a pressure cell;
    injecting, by an injection system in the pressure cell system, an injectable medium into the pressure cell in a gap between the sample and the inner walls;
    heating, by a heating element in the pressure cell system, the injectable medium in the pressure cell;
    measuring, by a pressure gauge in the pressure cell system, pressure inside the pressure cell;
    measuring, by a temperature gauge in the pressure cell system, a temperature in the pressure cell; and
    capturing, by a coaxial resonator system in the pressure cell system_through a short-circuited coaxial probe included in a high-pressure viewing window and connected to a coaxial resonator, microwave permittivity measurements of the sample at different combinations of temperatures and pressures, wherein the microwave measurements are captured after the sample is placed inside of the pressure cell and a top including a pressure resistant lid is closed on the pressure cell, after the injectable medium is injected into the pressure cell in the gap between the sample and the inner walls, and after heat is optionally provided by the heating element to the injectable medium in the pressure cell, wherein dimensions of a central conductor diameter and an outer diameter of a quartz window provide a coaxial line of a desired impedance of 50 ohm.

17. The non-transitory, computer-readable medium of claim 16, further comprising, when the sample is a fluid, measuring a permittivity of the injectable medium.

18. The non-transitory, computer-readable medium of claim 16, wherein the short-circuited coaxial probe is embedded in the inner walls of the pressure cell.

* * * * *

UNITED STATES PATENT AND TRADEMARK OFFICE
CERTIFICATE OF CORRECTION

PATENT NO. : 11,215,568 B2
APPLICATION NO. : 16/410634
DATED : January 4, 2022
INVENTOR(S) : Alvarez It is certified that error appears in the above-identified patent and that said Letters Patent is hereby corrected as shown below:

In the Claims

Column 15, Line 47, Claim 11, delete "Si'" and insert -- $S_{11}$ --;

Column 16, Line 42, Claim 16, delete "system_through" and insert -- system through --.

Signed and Sealed this
Twelfth Day of July, 2022

Katherine Kelly Vidal
*Director of the United States Patent and Trademark Office*